United States Patent [19]
Nabi et al.

[11] Patent Number: 4,894,220
[45] Date of Patent: Jan. 16, 1990

[54] ANTIBACTERIAL ANTIPLAQUE ORAL COMPOSITION

[75] Inventors: Nuran Nabi, North Brunswick; Abdul Gaffar, Princeton, both of N.J.

[73] Assignee: Colgate-Palmolive Company, New York, N.Y.

[21] Appl. No.: 291,712

[22] Filed: Dec. 29, 1988

Related U.S. Application Data

[63] Continuation-in-part of Ser. No. 8,901, Jan. 30, 1987.

[51] Int. Cl.$^4$ .......................... A61K 7/16; A61K 7/18; A61K 7/22
[52] U.S. Cl. .......................................... 424/52; 424/49; 424/54; 424/57
[58] Field of Search ..................................... 424/49–58

[56] References Cited

U.S. PATENT DOCUMENTS

| | | | |
|---|---|---|---|
| 4,656,031 | 4/1987 | Lane et al. | 424/49 |
| 4,749,561 | 6/1988 | Lane et al. | 424/49 |
| 4,749,562 | 6/1988 | Lane et al. | 424/49 |
| 4,767,751 | 8/1988 | Davis | 514/944 |

FOREIGN PATENT DOCUMENTS

| | | |
|---|---|---|
| 260859 | 3/1988 | European Pat. Off. . |
| 271332 | 6/1988 | European Pat. Off. . |
| 3802168 | 8/1988 | Fed. Rep. of Germany . |
| 7600817 | 8/1976 | Netherlands . |
| WO86/5391 | 9/1986 | PCT Int'l Appl. . |

Primary Examiner—Shep K. Rose
Attorney, Agent, or Firm—Robert L. Stone; Murray M. Grill

[57] ABSTRACT

An oral composition such as a dentifrice or mouthwash, containing an aqueous phase of water and as solubilizing agent propylene glycol, dipropylene glycol, methyl cellosolve, ethyl cellosolve, olive oil, castor oil, amyl acetate, ethyl acetate, glyceryl tristearate or benzyl benzoate mixed with at least one of glycerine and sorbitol, a substantially water-insoluble noncationic antibacterial antiplaque agent, such as 2,4,4'-trichloro-2$^1$-hydroxydiphenyl ether (triclosan), and a synthetic anionic linear polymeric polycarboxylate having a molecular weight of about 1,000 to about 1,000,000.

18 Claims, No Drawings

ANTIBACTERIAL ANTIPLAQUE ORAL COMPOSITION

This application is a continuation-in-part of application Ser. No. 07/008,901, filed Jan. 30, 1987.

This invention relates to an antibacterial antiplaque oral composition. More particularly, it relates to an oral composition containing a substantially water-insoluble noncationic antibacterial agent effective to inhibit plaque.

Dental plaque is a soft deposit which forms on teeth as opposed to calculus which is a hard calcified deposit on teeth. Unlike calculus, plaque may form on any part of the tooth surface, particularly including at the gingival margin. Hence, besides being unsightly, it is implicated in the occurence of gingivitis.

Accordingly, it is highly desirable to include antimicrobial agents which have been known to reduce plaque in oral compositions. Frequently, cationic antibacterial agents have been suggested. Moreover, in U.S. Pat. No. 4,022,880 to Vinson et al, a compound providing zinc ions as an anticalculus agent is admixed with an antibacterial agent effective to retard the growth of plaque bacteria. A wide variety of antibacterial agents are described with the zinc compounds including cationic materials such as guanides and quaternary ammonium compounds as well as non-cationic compounds such as halogenated salicylanilides and halogenated hydroxydiphenyl ethers. The noncationic antibacterial antiplaque halogenated hydrocydiphenyl ether, triclosan, has also been described in combination with zinc citrate trihydrate in European Patent Publication No. 0161,899 to Saxton et al.

The cationic antibacterial materials such as chlorhexidine, benzthonium chloride and cetyl pyridinium chloride have been the subject of greatest investigation as antibacterial antiplaque agents. However, they are not effective when used with anionic materials. Noncationic antibacterial materials, on the other hand, can be compatible with anionic components in an oral composition.

However, oral compositions typically are mixtures of numerous components and even such typically neutral materials as humectants can effect performance of such compositions.

It is an advantage of this invention that an oral composition containing a substantially water-insoluble noncationic antibacterial agent and a synthetic anionic linear polymeric polycarboxylate is provided to inhibit plaque formation.

It is an advantage of this invention that the polymeric polycarboxylates enhance the delivery and retention of the antibacterial agent on teeth and on soft oral tissues.

It is a further advantage of this invention that such an oral composition is provided with a humectant which dissolves the noncationic antibacterial agent is an essential component.

It is a further advantage of this invention that an antiplaque oral composition is provided which is effective to reduce the occurence of gingivitis.

Additional advantages of this invention will be apparent from consideration of the following specification.

In accordance with certain of its aspects, this invention relates to an oral composition comprising in an orally acceptable vehicle, a water-humectant phase, said water and humectant comprising at least about 10% by weight of said oral composition, an effective antiplaque amount of a substantially water insoluble noncationic antibacterial agent selected from the group consisting of halogenated diphenyl ethers and phenolic compounds and about 0.005–4% by weight of a synthetic anionic linear polymeric polycarboxylate having a molecular weight of about 1,000 to about 1,000,000, wherein said humectant includes a solubilizing agent selected from the group consisting of propylene glycol, dipropylene glycol, methyl cellosolve, ethyl cellosolve, olive oil, castor oil, amyl acetate, ethyl acetate, glyceryl tristearate and benzyl benzonate mixed with at least one of glycerine and sorbitol, the amount of said stabilizing agent being sufficient to dissolve said antibacterial agent.

Typical examples of water insoluble noncationic antibacterial agents which are particularly desirable from considerations of antiplaque effectiveness, safety and formulation are:

Halogenated Diphenyl Ethers

2',4,4'-trichloro-2-hydroxy-diphenyl ether (Triclosan)
2,2'-dihydroxy-5,5'-dibromo-diphenyl ether.

Phenolic Compounds (including phenol and its
homologs, mono- and poly-alkyl and aromatic
halophenols, resorcinol and its derivatives, bisphenolic
compounds and halogenated salicylanilides)

Phenol and its Homologs

Phenol

2 Methyl-Phenol
3 Methyl-Phenol
4 Methyl-Phenol
4 Ethyl-Phenol
2,4-Dimethyl-Phenol
2,5-Dimethyl-Phenol
3,4-Dimethyl-Phenol
2,6-Dimethyl-Phenol
4-n-Propyl-Phenol
4-n-Butyl-Phenol
4-n-Amyl-Phenol
4-tert-Amyl-Phenol
4-n-Hexyl-Phenol
4-n-Heptyl-Phenol Mono- and Poly-Alkyl and Aromatic Halophenols Methyl-p-Chlorophenol
Ethyl-p-Chlorophenol
n-Propyl-p-Chlorophenol
n-Butyl-p-Chlorophenol
n-Amyl-p-Chlorophenol
sec-Amyl-p-Chlorophenol
n-Hexyl-p-Chlorophenol
Cyclohexyl-p-Chlorophenol
n-Heptyl-p-Chlorophenol
n-Octyl-p-Chlorophenol O-Chlorophenol Methyl-o-Chlorophenol
Ethyl-o-Chlorophenol
n-Propyl-o-Chlorophenol
n-Butyl-o-Chlorophenol
n-Amyl-o-Chlorophenol
tert-Amyl-o-Chlorophenol
n-Hexyl-o-Chlorophenol
n-Heptyl-o-Chlorophenol p-Chlorophenol o-Benzyl-p-Chlorophenol
o-Benzyl-m-methyl-p-Chlorophenol
o-Benzyl-m, m-dimethyl-p-Chlorophenol
o-Phenylethyl-p-Chlorophenol
o-Phenylethyl-m-methyl-p-Chlorophenol
3-Methyl-p-Chlorophenol
3,5-Dimethyl-p-Chlorophenol
6-Ethyl-3-methyl-p-Chlorophenol
6-n-Propyl-3-methyl-p-Chlorophenol
6-iso-Propyl-3-methyl-p-Chlorophenol
2-Ethyl-3,5-dimethyl-p-Chlorophenol
6-sec Butyl-3-methyl-p-Chlorophenol
2-iso-Propyl-3,5-dimethyl-p-Chlorophenol
6-Diethylmethyl-3-methyl-p-Chlorophenol
6-iso-Propyl-2-ethyl-3-methyl-p-Chlorophenol
2-sec Amyl-3,5-dimethyl-p-Chlorophenol
2-Diethylmethyl-3,5-dimethyl-p-Chlorophenol
6-sec Octyl-3-methyl-p-Chlorophenol p-Bromophenol Methyl-p-Bromophenol
Ethyl-p-Bromophenol
n-Propyl-p-Bromophenol
n-Butyl-p-Bromophenol
n-Amyl-p-Bromophenol
sec-Amyl-p-Bromophenol
n-Hexyl-p-Bromophenol
cyclohexyl-p-Bromophenol o-Bromophenol tert-Amyl-o-Bromophenol
n-Hexyl-o-Bromophenol
n-Propyl-m,m-Dimethyl-o-Bromophenol 2-Phenyl Phenol 4-chloro-2-methyl phenol
4-chloro-3-methyl phenol
4-chloro-3,5-dimethyl phenol
2,4-dichloro-3,5-dimethylphenol
3,4,5,6-terabromo-2-methylphenol
5-methyl-2-pentylphenol
4-isopropyl-3-methylphenol
5-chloro-2-hydroxydiphenylemthane Resorcinol and its Derivatives Resorcinol Methyl-Resorcinol
Ethyl-Resorcinol
n-Propyl-Resorcinol
n-Butyl-Resorcinol
n-Amyl-Resorcinol
n-Hexyl-Resorcinol
n-Heptyl-Resorcinol
n-Octyl-Resorcinol
n-Nonyl-Resorcinol
Phenyl-Resorcinol
Benzyl-Resorcinol
Phenylethyl-Resorcinol
Phenylpropyl-Resorcinol
p-Chlorobenzyl-Resorcinol
5-Chloro-2,4-Dihydroxydiphenyl Methane
4'-Chloro-2,4-Dihydroxydiphenyl Methane
5-Bromo-2,4-Dihydroxydiphenyl Methane
4'-Bromo-2,4-Dihydroxydiphenyl Methane Bisphenolic Compounds 2,2'-methylene bis(4-chlorophenol)
2,2'-methylene bis(3,4,6-trichlorophenol)
2,2'-methylene bis(4-chloro-6-bromophenol)
bis(2-hydroxy-3,5-dichlorophenyl) sulfide
bis(2-hydroxy-5-chlorobenzyl) sulfide The noncationic antibacterial agent is present in the oral composition in an effective antiplaque amount, typically about 0.01-5% by weight preferably about 0.03-1% and most preferably about 0.3-0.5%. The antibacterial agent is substantially water-insoluble, meaning that its solubility is less than about 1% by weight in water at 25° C. and may be even less than about 0.1%.

The preferred halogenated diphenyl ether is triclosan. The preferred phenolic compounds are hexyl resorcinol, 2,2'-methylene bis(4-chloro-6-bromophenol) and Fluorophene. The most preferred antibacterial antiplaque compound is triclosan. Triclosan is disclosed in aforementioned U.S. Pat. No. 4,022,880 as an antibacterial agent in combination with an anticalculus agent which provides zinc ions. It is also disclosed as an antiplaque agent in a dentifrice formulated to contain a lamellar liquid crystal surfactant phase having a lamellar spacing of less than 6.0 mm and which may optionally contain a zinc salt in published European Patent Application 0161898 of Lane et al and in a dentifrice containing zinc citrate trihydrate in published European Patent Application 0161899 to Saxton et al.

Synthetic anionic polymeric polycarboxylate having a molecular weight of about 1,000 to about 1,000,000, preferably 30,000 to about 500,000, have been used in optimizing anticalculus effectiveness of linear molecularly dehydrated polyphosphate salts, as disclosed in U.S. Pat. No. 4,627,977 to Gaffar et al. It is further observed, in the context of the present invention that such polycarboxylate is effective to enhance delivery and retention of the nonionic antibacterial, antiplaque agent to dental surfaces.

The synthetic anionic polymeric polycarboxylate is an inhibitor of alkaline phosphatase enzyme. Synthetic anionic polymeric polycarboxylates and their complexes with various cationic germicides, zinc and magnesium have been previously disclosed as anticalculus agents per se in, for example U.S. Pat. No. 3,429,963 to Shedlovsky; U.S. Pat. No. 4,152,420 to Gaffar; U.S. Pat. No. 3,956,480 to Dichter et al; U.S. Pat. No. 4,138,477 to Gaffar; and U.S. Pat. No. 4,183,914 to Gaffar et al. It is to be understood that the synthetic anionic polymeric polycarboxylates so disclosed in these several patents are operative in the compositions and methods of this invention and such disclosures are to that extent incorporated herein by reference thereto.

The synthetic anionic polymeric polycarboxylates employed herein are well known, being often employed in the form of their free acids or preferably partially or more preferably fully neutralized water soluble alkali metal (e.g. potassium and preferably sodium) or ammonium salts. Preferred are 1:4 to 4:1 copolymers of maleic anhydride or acid with another polymerizable ethylenically unsaturated monomer, preferably methyl vinyl ether (maleic anhydride) having a molecular weight (M.W.) of about 30,000 to about 1,000,000, most preferably about 30,000 to about 500,000. These copolymers are available for example as Gantrez (AN 139 (M.W. 500,000), A.N. 119 (M.W. 250,000); and preferably S-97 Pharmaceutical Grade (M.W. 70,000), of GAF Corporation. The term "synthetic" is intended to exclude known thickening or gelling agents comprising carboxymethylcellulose and other derivatives of cellulose and natural gums.

Other operative polymeric polycarboxylates include those disclosed in U.S. Pat. No. 3,956,480 referred to above, such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Additional operative polymeric polycarboxylates disclosed in above referred to U.S. Pat. Nos. 4,138,477 and 4,183,914, include copolymers of maleic anhydride with styrene, isobutylene or ethyl vinyl ether, polyacrylic, polyitaconic and polymaleic acids, and sulfoacrylic oligomers of M.W. as low as 1,000, available as Uniroyal ND-2.

Suitable generally are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrilacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility.

Also useful herein are so-called carboxyvinyl polymers disclosed as toothpaste components in U.S. Pat. No. 3,980,767 to Chown et al; U.S. Pat. No. 3,935,306 to Roberts et al; U.S. Pat. No. 3,919,409 to Perla et al; U.S. Pat. No. 3,911,904 to Harrison, and U.S. Pat. No. 3,711,604 to Colodney et al. They are commercially available for example under the trademarks Carbopol 934, 940 and 941 of B. F. Goodrich, these products consisting essentially of a colloidally water-soluble polymer of polyacrylic acid crosslinked with from about 0.75% to about 2.0% of polyallyl sucrose or polyallyl pentaerythritol as cross linking agent.

The synthetic anionic polymeric polycarboxylate component is mainly a hydrocarbon with optional halogen and O-containing substituents and linkages as present in for example ester, ether and OH groups, and when present is employed in the instant compositions in approximate weight amounts of 0.05 to 4%, preferably 0.05 to 3%, more preferably 0.1 to 2%. Amounts in the upper portion of these ranges are typically employed in dentifrice compositions typically containing a dental abrasive and used in conjunction with brushing of the teeth, e.g. tooth pastes (including creams), gels, powders and tablets. Amounts in excess of these ranges may be employed for thickening or gelling purposes.

Without being bound to a theory, it is believed that the polymeric polycarboxylate is an anionic film forming material and is thought to attach to tooth surfaces and form a continuous film over the surfaces, thereby preventing bacterial attachment to tooth surfaces. It is possible that the noncationic antibacterial agent forms a complex with the polycarboxylate, thus forming a film of a complex of the two over tooth surfaces. The film forming property of the polycarboxylate and the enhanced delivery and film forming property of the polycarboxylate and the enhanced delivery and retention of the antibacterial agent on tooth surfaces due to the polycarboxylate appears to make tooth surfaces unfavourable for bacterial acumulation particularly since the direct bacteriostatic action of the antibacterial agent controls bacterial growth. Therefore, through the combination of three modes of actions: (1) enhanced delivery, (2) long retention time on tooth surfaces, and (3) prevention of bacterial attachment to tooth surfaces. The oral composition is made efficacious for reducing plaque.

In oral preparations such as mouthwashes and dentifrices, an orally acceptable vehicle including a water-phase with humectant is present. In the present invention, the water and humectant liquid phase comprises at least about 10% by weight of the oral preparation. Moreover, preferably propylene glycol, typically

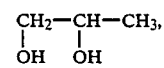

is present as a portion of the humectant to solubilize the substantially water-insoluble noncationic antibacterial agent. The remainder of the humectant is glycerine and/or sorbitol. Water is present typically in amount of at least about 3% by weight and glycerine and/or sorbitol typically total about 6.5-75% by weight of the oral preparation, more typically about 10-75%, and, together with the solubilizing humectant, the essential humectant components typically amount to about 7-80% by weight of the oral preparation. Reference hereto to sorbitol refers to the material typically as available commercially in 70% aqueous solutions. Significant amounts of polyethylene glycol particularly of molecular weight of 600 or more should be avoided since polyethylene glycol effectively inhibits the antibacterial activity of the noncationic antibacterial agent even when propylene glycol is present to effect its solubilization. For instance, polyethylene glycol (PEG) 600 when present with triclosan in a weight ratio of 25 triclosan:1 PEG 600 reduces the antibacterial activity of triclosan by a factor of about 16 from that prevailing in the absence of the polyethylene glycol.

Besides the preferred solubilizing humectant, propylene glycol, other solubilizing agent which do not adversely affect the antibacterial activity may be used. These are dipropylene glycol, methyl cellosolve, ethyl cellosolve, olive oil, castor oil, amyl acetate, ethyl acetate, glyceryl tristearate and benzyl benzoate.

When the amount of substanially water-soluble noncationic antibacterial agent is low, say up to about 0.3% by weight, as little as about 0.5% by weight of the solubilizing humectant can be sufficient to solubilize the antibacterial agent. When higher amounts of antibacterial are present, it is desirable that at least about 5% by weight of the solubilizing humectant be present.

In certain highly preferred forms of the invention the oral composition may be substantially liquid in character, such as a mouthwash or rinse. In such a preparation the vehicle, in addition to the humectant, is typically a water-alcohol mixture. Generally, the weight ratio of water to alcohol is in the range of from about 1:1 to about 20:1, preferably about 3:1 to 10:1 and more preferably about 4:1 to about 6:1. The total amount of water-alcohol mixture in this type of preparation is typically in the range of from about 70 to about 99.9% by weight of the preparation with the humectant typically being about 10–29.9% by weight, preferably about 0.5–15% by weight of propylene glycol and about 9.5–24.9% by weight of glycerine and/or sorbitol. The alcohol being non-toxic in nature is typically ethanol or isopropanol. Ethanol is preferred.

The pH of such liquid and other preparation of the invention is generally in the range of about 4.5 to about 9 or 10 and most preferably about 6.5 to about 7.5 It is noteworthy that the compositions of the invention may be applied orally at a pH below 5 without substantially decalcifying or otherwise damaging dental enamel. The pH can be controlled with acid (e.g. citric acid or benzoic acid) or base (e.g. sodium hydroxide) or buffered (as with sodium citrate, benzoate, carbonate, or bicarbonate, disodium hydrogen phosphate, sodium dihydrogen phosphate, etc.).

In certain other desirable forms of this invention, the oral composition may be substantially pasty in character, such as a dentifrice, that is a toothpaste (dental cream) or gel dentifrice. The vehicle of such pasty oral preparations generally contains dentally acceptable polishing material. Examples of polishing materials are water-insoluble sodium metaphosphate, potassium metaphosphate, tricalcium phosphate, dihydrated calcium phosphate, anhydrous dicalcium phosphate, calcium pyrophosphate, magnesium orthophosphate, trimagnesium phosphate, calcium carbonate, aluminum silicate, zirconium silicate, silica, bentonite, and mixtures thereof. Other suitable polishing material include the particulate thermosetting resins described in U.S. Pat. No. 3,070,510 of Dec. 15, 1962 such as melamine-, phenolic, and urea-formaldehydes, and cross-linked polyepoxides and polyesters. Preferred polishing materials include crystalline silica having particle sized of up to about 5 microns, a mean particle size of up to about 1.1 microns, and a surface area of up to about 50,000 cm.$^2$/gm., silica gel or colloidal silica, and complex amorphous alkali metal aluminosilicate.

When visually clear or opacified gels are employed, a polishing agent of colloidal silica, such as those sold under the trademark SYLOID as Syloid 72 and Syloid 74 or under the trademark SANTOCEL as Santocel 100 or alkali metal almuino-silicate complexes are particularly useful, since they are consistent with gel-like texture and have refractive indices close to the refractive indices of gelling agent-liquid (including water and/or humectant)systems commonly used in dentifices.

Many of the so-called "water-insoluble" polishing materials are anionic in character and also include small amounts of soluble material. Thus, insoluble sodium metaphosphate may be formed in any suitable manner as illustrated by Thorpe's Dictionary of Applied Chemistry, Volume 9, 4th Edition, pp. 510–511. The forms of insoluble sodium metaphosphate known as Madrell's salt and Kurrol's salt are further examples of suitable materials. These metaphosphate salts exhibit only a minute solubility in water, and therefore are commonly referred to as insoluble metaphosphates (IMP). There is present therein a minor amount of soluble phosphate material as impurities, usually a few percent such as up to 4% by weight. The amount of soluble phosphate material, which is believed to include a soluble sodium trimetaphosphate in the case of insoluble metaphosphate, may be reduced or eliminated by washing with water if desired. The insoluble alkali metal metaphosphate is typically employed in powder form of a particle size such that no more than 1% of the material is larger than 37 microns.

The polishing material is generally present in the cream paste or gel compositions in weight concentrations of about 10% to about 75%.

In a toothpaste, the liquid vehicle may typically comprise about 10–35% by weight of water and the solubilizing agent (e.g. propylene glycol) with glycerine and/or sorbitol humectant in an amount ranging from about 10% to about 80% by weight of the preparation the amount of propylene glycol typically being about 0.5–20% by weight. In clear gels where the refractive index is an important consideration, about 3–30% of water, about 0.5–20% of solubilizing humectant (e.g. propylene glycol), 0 to about 70% of glycerine and about 20–25% of sorbitol are preferably employed.

Toothpastes, creams and gels typically contain a natural or synthetic thickener or gelling agent in proportions of about 0.1 to about 10, preferably about 0.5 to about 5%. A suitable thickener is synthetic hectorite, a synthetic colloidal magnesium alkali metal silicate complex clay available for example as Laponite (e.g. CP, SP 2002, D) marketed by Laporte Industries Limited. Laponite D analysis shows, approximately by weight, 58.00% $SiO_2$, 25.40% MgO, 3.05% $Na_2O$, 0.98% $Li_2O$, and some water and trace metals. Its true specific gravity is 2.53 and it has an apparent bulk density (g./ml. at 8% moisture) of 1.0.

Other suitable thickeners include Irish moss, i-carreageenan, gum tragacanth, starch, polyvinylpyrrolidone, hydroxyethypropylcellulose, hydroxybutyl methyl cellulose, hydroxypropyl methyl cellulose, hydroxyethyl cellulose (e.g. available as Natrosol), sodium carboxymethyl cellulose, and colloidal silica such those available as finely ground Syloid (244) and Sylodent 15.

Since there maybe a tendency for the dentifrice to separate into liquid and solid portions when about 5% by weight or more of solubilizing agent such as propylene glycol is present and since excellent antiplaque and adhesion effects can be obtained with small amounts of antibacterial agent which do not require so much solubilizing agent to effect solubilization, a preferred dentifrice contains about 0.3% by weight of the antibacterial agent, about 1.5–2% by weight of the polycarboxylate and about 0.5%–1% by weight of the solubilizing agent.

Without being bound to a theory whereby the advantages of this invention are achieved, is believed that an aqueous, humectant vehicle is normally solubilized in surfactant micelles in the mobile phase (that is, not including gelling agent and polishing agent) of a dentfrice formula or in a mouthrinse. The mouthrinse or mobile phase solution of dentifrice during use becomes diluted with saliva and triclosan would precipitate out without the presence of highly solubilizing humectant. On the other hand, propylene glycol being a strong solubilizing agent for triclosan, appears to prevent such a situation and permit continued humectant presence with triclosan. In this regard it is noted that propylene glycol is widely used in drug delivery systems for its strong interaction with biological membranes. It is expected that triclosan is partitioned from aqueous environment into propylene glycol and surfactant emulsions during use and further that propylene glycol in bulk phase allows greater probability of triclosan emergence out of surfactant micelles, thereby rendering triclosan available for delivery into bacterial and soft surfaces as well as onto tooth surfaces. Similar remarks would apply to other water-insoluble noncationic antibacterial agents herein described.

In accordance with a further aspect of the invention anticalculus properties may also be provided to the oral composition by the inclusion of a molecularly dehydrated polyphosphate salt.

The linear molecularly dehydrated polyphosphate salts operative herein as anticalculus agents are well known, being generally employed in the form of their wholly or partially neutralized water soluble alkali metal (e.g. potassium and preferably sodium) or ammonium salts, and any mixtures thereof. Representative examples include sodium hexametaphosphate, sodium tripolyphosphate, disodium diacid, trisodium monoacid and tetrasodium pyrophosphates and the like. Linear polyphosphates correspond to $(NaPO_3)n$ where n is about 2 to about 125. They are generally employed in the instant oral compositions in approximate weight amounts of 0.1 to 7% preferably 1 to 7%, more preferably 2 to 7%. When n is at least 3 in $(NaPO_3)n$, the polyphosphates are glassy in character.

Particularly desirable anticalculus agents are tetraalkali metal pyrophosphates, including mixtures thereof, such as tetrasodium pyrophosphate tetraposition pyrophosphate and mixtures thereof. An anticalculus agent comprising about 4.3% to about 7% by weight of the oral compositions where in the weight ratio of tetrapotassium pyrophosphate to tetrasodium pyrophosphate is from about 4.3:2.7 to about 6:1 is especially preferred.

In order to optimize the anticalculus effectiveness of the oral composition, inhibitors against enzymatic hydrolysis of the polyphosphate are desirably present. The synthetic anionic polymeric polycarboxylate as described is one such agent. The other is an amount of a fluoride ion source sufficient to supply 25 ppm. to 5,000 ppm. of fluoride ions. The fluoride ion source may be present even when the polyphosphate anticalculus agent is not, since it also provides anticaries effectiveness.

The sources of fluoride ions, or fluorine-providing component, as anti-caries as well as acid phosphates and pyrophosphatase enzyme inhibitor component, are well known in the art as anti-caries agents. These compounds may be slightly soluble in water or may be fully water-soluble. They are characterized by their ability to release fluoride ions in water and by freedom from undesired reaction with other compounds of the oral preparation. Among these materials are inorganic fluoride salts, such as soluble alkali metal, alkaline earth metal salts, or example, sodium fluoride, potassium fluoride, ammonium fluoride, calcium fluoride, a copper fluoride such as cuprous fluoride, zinc fluoride, barium fluoride, sodium flourosilicate, ammonium flourosilicate, sodium fluorozirconate, sodium fluorozirconate, sodium monofluorphosphate, aliminum mono- and di-fluorophosphate, and fluorinated sodium calcium pyrophosphate. Alkali metal and tin fluorides, such as sodium and stannous fluorides, sodium monofluorophosphate (MFP) and mixtures thereof, are preferred.

The amount of fluorine-providing compound is dependent to some extent upon the type of compound, its solubility, and the type of oral preparation, but it must be a non-toxic amount, generally about 0.0005 to about 3.0% in the preparation. In a dentifrice preparation, e.g. dental gel and toothpaste (including cream), an amount of such compound which releases up to about 5,000 ppm of F ion by weight of the preparation is considered satisfactory. Any suitable minimum amount of such compound may be used, but it is preferable to employ sufficient compound to release about 300 to 2,000 ppm, more preferable about 800 to about 1,500 ppm of fluoride ion.

Typically, in the cases of alkali metal fluorides, this component is present in an amount up to about 2% by weight, based on the weight of the preparation, and preferably in the range of about 0.05% to 1%. In the case of sodium monofluorophosphate, the compound may e present in an amount of about 0.1–3%, more typically about 0.76%.

It will be understood that, as is conventional, the oral preparations are to be sold or otherwise distributed in suitable labelled packages. Thus a jar of mouthrinse will have a label describing it, in substance, as a mouthrinse or mouthwash and having directions for its use; and a toothpaste, cream or gel will usually be in a collapsible tube, typically aluminum, lined lead or plastic, or other squeeze, pump or pressurized dispenser for metering out the contents, having a label describing it, in substance, as a toothpaste, gel or dental cream.

Organic surface-active agents are used in the compositions of the present invention to achieve increased prophylactic action, assist in achieving thorough and complete dispersion of the anticalculus agent throughout the oral cavity, and render the instant compositions more cosmetically acceptable. The organic surface-active material is preferably anionic, nonionic or ampholytic in nature, and it is preferred to employ as the surface-active agent a detersive material which imparts to the composition detersive and foaming properties. Suitable examples of anionic surfactants are water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkyl sulfoacetates, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmitoyl sacrosine which should be substantially free from soap or similar higher fatty acid material. The use of these sarcosinate compounds in the oral compositions of the present invention is particularly advantageous since these materials exhibit a prolonged and marked effect in the inhibition of acid formation in the oral cavity due to carbohydrate breakdown in addition to exerting some reduction in the solubility of tooth enamel in acid solutions. Examples of water-soluble nonionic surfactants are condensation products of ethylene oxide with various reactive hydrogen-containing compounds reactive therewith having long hydrophobic chains (e.g. aliphatic chains of about 12 to 20 carbon atoms), which condensation products ("ethoxamers") contain hydrophilic polyoxyethylene moieties, such as condensation products of poly(ethylene oxide) with fatty acids, fatty alcohols, fatty amides, polyhydric alcohols (e.g. sorbitan monosterate) and polypropyleneoxide (e.g. Pluronic materials).

Surface active agent is typically present in amount of about 0.5–5% by weight, preferably about 1–2%. It is noteworthy, that surface active agent can assist in the dissolving of the noncationic antibacterial agent and thereby diminish the amount of solubilizing humectant needed.

Various other materials may be incorporated in the oral preparations of this invention such as whitening agents, preservatives, silicones, chlorophyll compounds and/or ammoniated material such as urea, diammonium phosphate, and mixtures thereof. These adjuvants, where present, are incorporated in the preparations in amounts which do not substantially adversely affect the properties and characteristics desired. Significant amounts of zinc, magnesium and other metal salts and materials, generally soluble, which would complex with active components of the instant invention are to be avoided.

Any suitable flavoring or sweetening material may also be employed. Examples of suitable flavoring constituents are flavoring oils, e.g. oil of spearmint, peppermint, wintergreen, sassafras, clove, sage, eucalyptus, marjoram, cinnamon, lemon, and orange, and methyl salicylate. Suitable sweetening agents include sucrose, lactose, maltose, xylitol, sodium cyclamate, perillartine, AMP (aspartyl phenyl alanine, methyl ester), saccharine and the like. Suitably, flavor and sweetening agents may together comprise from about 0.1% to 5% more of the preparation.

In the preferred practice of this invention an oral composition according to this invention such as a mouthwash or dentifrice containing the composition of the present invention is preferably applied regularly to dental enamel, such as every day or every second or third day or preferably from 1 to 3 times daily, at a pH of about 4.5 to about 9, generally about 5.5 to about 8, preferably about 6 to 8, for at least 2 weeks up to 8 weeks or more up to lifetime.

The following examples are further illustrative of the nature of the present invention, but it is understood that the invention is not limited thereto. All amounts and proportions referred to herein and in the appended claims are by weight, unless otherwise indicated.

EXAMPLE 1

The effect of synthetic anionic linear polycarboxylate on the uptake, retention to and release from tooth surfaces of water-insoluble noncationic antibacterial agent is assessed in vitro on a saliva coated hydroxyapatite disk and on exfoliated buccal epithelial cells. The in vitro assessments are correlatable to in vivo plaque measurements and in vitro reduction is indicative of in vivo reduction.

Dentifrices prepared having the following formulas:

|  | Parts | |
|---|---|---|
|  | A | B |
| Propylene Glycol | 10.00 | 10.00 |
| Iota Carrageenan | 0.75 | 0.75 |
| Gantrez S-97 | — | 2.00 |
| Titanium Dioxide | 0.50 | 0.50 |
| Sorbitol (70%) | 30.00 | 30.00 |
| Sodium Fluoride | 0.332 | 0.332 |
| Sodium Saccharin | 0.40 | 0.40 |
| Silica Thickener (Sylodent 15) | 3.00 | 3.00 |
| Silica Polishing Agent (Zeodent 113) | 20.00 | 20.00 |
| Triclosan | 0.20 | 0.20 |
| Sodium Lauryl Sulfate | 2.00 | 2.00 |
| Flavor | 0.95 | 9.95 |
| Ethyl Alcohol | 1.00 | 1.00 |
| Sodium Hydroxide (50%) | 0.80 | 0.80 |
| Water | Q.S. to 100.0 | Q.S. to 100.0 |

The uptake of triclosan on the saliva coated hydroxyapatite disk and on buccal epithelial cells with varying levels of the polymeric polycarboxylate, Gantrez S-97, is set forth in Table 1 below:

TABLE 1

| Dentifrice | Uptake of Triclosan in micrograms On Saliva Coated Disk | In Micrograms $\times 10^5$ Buccal Epithelical Cells |
|---|---|---|
| A | 25.0 | 38.0 |
| B | 54.0 | 96.0 |

These results reveal that the Gantrez material greatly enhances the delivery and uptake of triclosan to saliva coated hydroxyapatite disk and to the exfoliated buccal epithelical cells.

Similar results are obtained when the dentifrices contain 3% of tricolosan.

EXAMPLE 2

In separate tests with saliva coated hydroxapatite disks and exfoliated buccal epithelical cells from those set forth in Example 1 above, dentifrice B containing 2.00% Gantrez S-97 and 0.20% of triclosan, 10.00% of propylene glycol and 2.00% of sodium lauryl sulfate and an equivalently formulated dentifrice, except for the presence of 0.30% of triclosan (Dentifrice B') were compared with a commercially available dentifrice containing (a) 0.2% of triclosan, (b) no Gantrez material, (c) no propylene glycol, (d) 0.5% zinc citrate, (e) 2.5% of surface active agents (f) sodium monofluorophosphate and hydrated alumina polishing agent (Dentifrice C); and the dentifrice formulation below (Dentifrice C') which is similar to commercial Dentifrice C except for the presence of 0.30% of troclosan:

|  | % |
|---|---|
| Sorbitol (70%) | 27.00 |
| Sodium Carboxymethyl Cellulose | 0.80 |
| Sodium Monofluorophosphate | 0.85 |
| Zinc Citrate | 0.50 |
| Sodium Saccharin | 0.18 |
| Water | 16.47 |
| Hydrated Alumina Polishing Agent | 50.00 |
| Ethanol | 0.20 |
| Sodium Lauryl Sulfate | 1.875 |
| Sodium Dodecyl Benzene Sulfonate | 0.625 |
| Triclosan | 0.30 |
| Flavor | 1.20 |

Since Dentifrices C and C' contain a total of 2.50% of surface active agent, more surface active agent is available to dissolve triclosan than in Dentifrices B and B' which contain 2.00%. However, propylene glycol in Dentifrices B and B' insures optimum dissolution of triclosan.

The advantage of Dentifrices B and B' over Dentifrices C and C' in triclosan uptake on saliva coated hydroxyapatite disks and on exfoliated buccal epithelial cells is shown in the Table 2 below:

TABLE 2

| | | Delivery of Triclosan | |
|---|---|---|---|
| | | To Saliva Coated Hydroxyapatite Disk (in micrograms) | To Buccal Epithelial Cells in micrograms × $10^6$ Epithelial Cells |
| Dentifrice | B | 41.1 | 101.6 |
| | B' | 77.4 | 142.0 |
| | C | 20.4 | 61.0 |
| | C' | 42.6 | 100.0 |

These results indicate that dentifrices containing triclosan, Gantrez material and propylene glycol can provide enhanced delivery of triclosan to tooth surfaces and soft surfaces in the oral cavity, thereby providing improved antiplaque and antibacterial effects.

EXAMPLE 3

For purpose of comparison, Formulas A, B and C, below are prepared:

Formula A is a tartar control dentifrice (containing testrosodium pyrophosphate, sodium fluoride and a Gantrez polycarboxylate, with triclosan as an antibacterial antiplaque agent and with a humectant system of glycerine and sorbitol.

Formula B is a similar type tartar control dentrifice except that in the humectant system, propylene glycol is present with sorbitol.

Formula C is similar to Formula B except principally that the pyrophosphate anticalculus agent is not present.

| | A % | B % | C % |
|---|---|---|---|
| Glycerin | 10.00 | — | — |
| Propylene Glycol | — | 10.00 | 10.00 |
| Iota Carrageenan | 0.750 | 0.60 | 0.60 |
| Sorbitol (70%) | 30.00 | 25.00 | 25.00 |
| Sodium Saccharin | 0.300 | 0.40 | 0.40 |
| Sodium Fluoride | 0.243 | 0.243 | 0.243 |
| Titanium Dioxide | 0.500 | 0.50 | 0.50 |
| Tetrasodium Pyrophosphate | 2.00 | 2.00 | — |
| Gantrez S-97 | 1.50 | 2.00 | 2.00 |
| Water | 26.107 | 26.657 | 28.657 |
| NaOH(50%) | 1.500 | 2.00 | 2.00 |
| Zeodent 113(Silica Polishing Agent) | 20.00 | 20.00 | 20.00 |
| Sylodent 15 (Silica Thickener) | 3.00 | 5.50 | 5.50 |
| Flavor | 1.10 | 1.10 | 1.10 |
| Triclosan | 0.50 | 0.50 | 0.50 |
| Sodium Lauryl Sulfate | 2.50 | 2.50 | 2.50 |
| Ethanol | — | 1.00 | 1.00 |
| | pH 7.9 | pH 7.0 | pH 7.0 |

The uptake of triclosan from each of dentifrice A, B and (C) is determined on saliva coated hydroxyapatite disk (4 for each dentifrice) with slurries of 50% of dentifrice as indicated in Table 3 below:

TABLE 3

| Dentifrice Slurry | Uptake of Triclosan Micrograms/Disk |
|---|---|
| A | 1.6 + 0.3 |
| B | 19.1 + 3 |
| C | 99.9 + 21 |

The foregoing results reveal improvements of about 11 and 61 times in triclosan uptake with anticalculus, antiplaque dentifrice B and antiplaque dentifrice C, each containing propylene glycol, over that achieved with dentifrice A containing no propylene glycol.

Additional experiments with a 50% slurry of dentifrice C to determine the retention of triclosan on the saliva coated hydroxyapatite disk over a period of time reveals retention of excellent levels of triclosan as shown in Table 4, below:

TABLE 4

Retention of Triclosan Adsorption from Dentifrice C Slurry

| Time (in Minutes) | Uptake of Triclosan (Micrograms/Disk) |
|---|---|
| 0 | 70 |
| 30 | 60 |
| 60 | 70 |
| 120 | 65 |
| 180 | 57 |
| 240 | 59 |

EXAMPLE 4

An "in-house" study was conducted on a group of volunteers to assess the effects of particular toothpastes in influencing plaque regrowth in accordance with the method described by Addy, Willis and Moran, J. Clin. Paerio., 1983, Vol. 10, Pages 89–99. The toothpastes tested included a placebo control (1), a control containing 0.3% of triclosan and 1.5% of Gantrez S-97 with glycerine and sorbitol as humectant (2) and a toothpaste in accordance with this invention containing 0.3% of triclosan, 2% of Gantrez S-97 and humectant of propylene glycol and sorbitol. The formulas of toothpastes (1), (2) and (3) are as follows:

| | Parts | | |
|---|---|---|---|
| | (1) Placebo | (2) Control | (3) Invention |
| Polyethylene Glycol 600 | 3.00 | | |
| Glycerine | 25.00 | 10.00 | |
| Propylene Glycol | | | 10.00 |
| Sorbitol (70%) | 41.617 | 30.00 | 25.00 |
| Sodium Carboxymethyl Cellulose | 0.35 | | |
| Iota Carrageenan | | 0.75 | 0.60 |
| Sodium Benzoate | 0.50 | | |
| Sodium Saccharin | 0.20 | 0.30 | 0.40 |
| Sodium Fluoride | 0.243 | 0.243 | 0.243 |
| Silica Polishing Agent (Zeodent 113) | 18.00 | 20.00 | 20.00 |
| Silica thickener (Sylox 15) | 5.50 | | 5.50 |
| (Sylodent 15) | | 3.00 | |
| Water | 3.00 | 26.307 | 26.857 |
| Gantrez S-97 | | 1.50 | 2.00 |
| Tetrasodium pyrophosphate | | 2.00 | |
| Triclosan | | 0.30 | 0.30 |
| Titanium Dioxide | 0.50 | 0.50 | 0.50 |
| Sodium Lauryl Sulfate | 1.20 | 2.50 | 2.50 |
| Flavor | 0.89 | 1.10 | 1.10 |
| Ethyl Alcohol | | | 1.00 |
| Sodium Hydroxide (50%) | | | 2.00 |
| pH | | 7.9 | 7.0 |

With regard to plaque reduction, on the teeth of the volunteers, compared to placebo (1), toothpaste (2) provided only a non-significant reduction of 8% while toothpaste (3) provided a significant decrease of 20%.

Since lesser amounts of propylene glycol can dissolve the 0.3 parts of triclosan present in Toothpaste (3), similar results are expected when the amount of propylene glycol is reduced to 0.5 parts and the amount of sorbitol is increased to 39.5 parts. Likewise, propylene glycol can be replaced by any of dipropylene glycol, methyl cellosolve, ethyl cellosolve, olive oil, castor oil, amyl acetate, ethyl acetate, glyceryl tristearate or benzyl benzoate.

EXAMPLE 5

The mouthrinses below are effective in reducing plaque.

Mouthrinse A is also effective in reducing caries and calculus.

|  | A Parts | B Parts |
|---|---|---|
| Tetrasodium Pyrophosphate | 2.00 | — |
| Gantrez S-97 | 0.25 | 0.25 |
| Glycerine | 10.00 | 10.00 |
| Propylene Glycol | 5.00 | 5.00 |
| Sodium Fluoride | 0.05 | — |
| Pluronic F108 (Polyoxyethylene/Polyoxypropylene Block Copolymer) | 2.00 | 2.00 |
| Triclosan | 0.10 | 0.10 |
| Flavor | 0.40 | 0.40 |
| Water | Q.S. to 100.00 | Q.S. to 100.00 |

In the foregoing examples, other antibacterial agents herein described such as 2-methyl phenol, methyl-p-chlorophenol and n-hexyl resorcinol may replace triclosan. Likewise, polymeric polycarboxylate other than Gantrez S-97, such as 1:1 copolymer of maleic anhyride and ethyl acrylate and sulfoacrylic oligomers, may be used.

This invention has been described with respect to certain preferred embodiments and it will be understood that modifications and variations thereof obvious to those skilled in the art are to be included within the purview of this application and the scope of the appended claims.

We claim:

1. An oral composition comprising in an orally acceptable vehicle, a water-humectant phase, said water and humectant comprising at least about 10% by weight of said oral composition, an efective antiplaque amount of a substantially water insoluble noncationic antibacterial agent selected from the group consisting of halogenated diphenyl ethers and about 0.0005-4% by weight of a systematic anionic linear polymeric polycarboxylate having a molecular weight of about 1,000 to about 1,000,000, wherein said humectant includes a solubilizing agent selected from the group consisting of propylene glycol, dipropylene glycol, methyl cellosolve, ethyl cellosolve, olive oil, castor oil, amyl acetate, ethyl acetate, glyceryl tristearate and benzyl benzoate mixed with at least one of glycerine and sorbitol, the amount of said solubilizing humectant being sufficient to dissolve said antibacterial agent.

2. The oral composition claimed in claim 1 containing about 0.5-50% by weight of propylene glycol.

3. The oral composition claimed in claim 2 containing about 0.01-5% by weight of said antibacterial agent, wherein said antibacterial agent is a halogenated diphenyl ether.

4. The oral composition claimed in claim 3 wherein said antibacterial agent is present in amount of about 0.1-0.5%.

5. The oral composition claimed in claim 3 wherein said halogenated diphenyl ether is 2,4,4'-trichloro-2-hydroxy-diphenyl ether.

6. The oral composition claimed in claim 1 wherein said polymeric polycarboxylate is present in amount of about 0.1 to 2% of a water soluble alkali metal or ammonium salt of a copolymer of vinyl methyl ether and maleic acid or anhydride having a molecular weight of about 30,000 to about 500,000.

7. The oral composition claimed in claim 1 containing an effective anticalculus amount of material comprising at least one linear molecularly dehydrated polyphosphate salt as essential anticalculus agent.

8. The oral composition claimed in claim 7 wherein said polyphosphate salt is present in amount of about 0.1-7% by weight and is tetrasodium pyrophosphate.

9. The oral composition in claim 7 wherein said composition contains an amount of fluoride ion source sufficient to supply 25 ppm. to 2,000 ppm. of fluoride ions.

10. The oral composition claimed in claim 7 wherein said fluoride source is sodium fluoride.

11. The oral composition claimed in claim 1 wherein said composition contains an amount of fluoride ion source sufficient to supply 25 ppm to 2000 ppm of fluoride ions.

12. The oral composition claimed in claim 1 wherein said oral composition contains a dentally acceptable water-insoluble polishing agent and said oral compositions is a toothpaste or dentifrice.

13. The oral composition claimed in claim 12 wherein said oral composition contains about 0.5-50% by weight of propylene glycol about 0.1-10% by weight a gelling agent and about 10-75% by weight of said polishing agent and said oral composition is a toothpaste or gel dentifrice.

14. The oral composition claimed in claim 13 wherein about 0.3% by weight of said antibacterial agent is present, about 0.1.5-2% by weight of said polycarboxylate is present and about 0.5-1% by weight of propylene glycol is present.

15. The oral composition claimed in claim 13 wherein said polishing material is a silica polishing material.

16. The oral composition claimed in claim 1 wherein said oral composition contains about 70-99.9% by weight of a mixture of water and alcohol in a weight ratio of from about 1:1 to about 20:1 and said oral composition is a mouthrinse.

17. The oral composition claimed in claim 16 wherein said alcohol is ethanol.

18. The oral composition claimed in claim 16 wherein about 5-20% by weight of propylene glycol is present.

* * * * *

UNITED STATES PATENT AND TRADEMARK OFFICE
CERTIFICATE OF CORRECTION

PATENT NO. : 4,894,220

DATED : January 16, 1990

INVENTOR(S) : Nuran Nabi and Abdul Gaffar

It is certified that error appears in the above—identified patent and that said Letters Patent is hereby corrected as shown below:

Column 5, Line 58, change " "0.05 to 4% to -- 0.005 to 4%--.

Column 15, Line 47 (in Claim 1) change "0.0005 - 4%" to --0.005 - 4%--.

Column 15 Line 48, change "systematic" to --synthetic--.

Signed and Sealed this

Ninth Day of April, 1991

Attest:

HARRY F. MANBECK, JR.

*Attesting Officer*     *Commissioner of Patents and Trademarks*